(12) United States Patent
McKenna

(10) Patent No.: US 8,818,473 B2
(45) Date of Patent: Aug. 26, 2014

(54) ORGANIC LIGHT EMITTING DIODES AND PHOTODETECTORS

(75) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 703 days.

(21) Appl. No.: 12/956,950

(22) Filed: Nov. 30, 2010

(65) Prior Publication Data

US 2012/0136227 A1 May 31, 2012

(51) Int. Cl.
*A61B 5/1455* (2006.01)

(52) U.S. Cl.
USPC ............................ 600/323; 600/310; 600/322

(58) Field of Classification Search
USPC ................................................ 600/309–344
See application file for complete search history.

(56) References Cited

U.S. PATENT DOCUMENTS

| | | | |
|---|---|---|---|
| 4,223,680 A | 9/1980 | Jobsis | |
| 4,281,645 A | 8/1981 | Jobsis | |
| 5,088,493 A | 2/1992 | Giannini et al. | |
| 5,239,185 A | 8/1993 | Ito et al. | |
| 5,279,295 A | 1/1994 | Martens et al. | |
| 5,299,570 A | 4/1994 | Hatschek | |
| 5,361,758 A | 11/1994 | Hall et al. | |
| 5,413,100 A | 5/1995 | Barthelemy et al. | |
| 5,575,285 A | 11/1996 | Takanashi et al. | |
| 5,596,986 A | 1/1997 | Goldfarb | |
| 5,632,273 A | 5/1997 | Suzuki | |
| 5,766,127 A | 6/1998 | Pologe et al. | |
| 5,823,950 A | 10/1998 | Diab et al. | |
| 5,917,280 A * | 6/1999 | Burrows et al. | 313/506 |
| 5,922,607 A | 7/1999 | Bernreuter | |
| 5,983,122 A | 11/1999 | Jarman et al. | |
| 5,994,836 A | 11/1999 | Boer et al. | |
| 6,031,603 A | 2/2000 | Fine et al. | |
| 6,064,898 A | 5/2000 | Aldrich | |
| 6,064,899 A | 5/2000 | Fein et al. | |
| 6,078,833 A | 6/2000 | Hueber | |
| 6,097,147 A | 8/2000 | Baldo et al. | |
| 6,337,492 B1 | 1/2002 | Jones et al. | |
| 6,483,099 B1 * | 11/2002 | Yu et al. | 250/214.1 |
| 6,587,703 B2 | 7/2003 | Cheng et al. | |

(Continued)

FOREIGN PATENT DOCUMENTS

CN    1540314 A    10/2004
CN    2691489 Y    4/2005

(Continued)

OTHER PUBLICATIONS

DeKock, Marc; "Pulse Oximetry Probe Adhesive Disks: A Potential for Infant Aspiration," Anesthesiology, vol. 89, pp. 1603-1604 (1998).

(Continued)

*Primary Examiner* — Eric Winakur
*Assistant Examiner* — Marjan Fardanesh
(74) *Attorney, Agent, or Firm* — Fletcher Yoder PC

(57) ABSTRACT

A system and method for determining physiological parameters of a patient based on light transmitted through the patient. The light may be transmitted via a broadband light source and received by a detector. The light may be selectively detected at a detector. Based on material characteristic of the detector, specific wavelengths of light are detected by the detector for use in monitoring the physiological parameters of the patient.

20 Claims, 4 Drawing Sheets

(56) References Cited

U.S. PATENT DOCUMENTS

| | | |
|---|---|---|
| 6,594,513 B1 | 7/2003 | Jobsis et al. |
| 6,597,931 B1 | 7/2003 | Cheng et al. |
| 6,615,064 B1 | 9/2003 | Aldrich |
| 6,671,526 B1 | 12/2003 | Aoyagi et al. |
| 6,842,635 B1 | 1/2005 | Parker |
| 7,027,849 B2 | 4/2006 | Al-Ali |
| 7,221,969 B2 | 5/2007 | Stoddart et al. |
| 7,230,608 B2 | 6/2007 | Cok |
| 7,283,242 B2 | 10/2007 | Thornton |
| 7,319,894 B2 | 1/2008 | Higgins |
| 7,330,746 B2 | 2/2008 | Demuth et al. |
| 7,349,726 B2 | 3/2008 | Casciani et al. |
| 7,376,454 B2 | 5/2008 | Casciani et al. |
| 7,415,298 B2 | 8/2008 | Casciani et al. |
| 7,424,317 B2 | 9/2008 | Parker et al. |
| 8,315,682 B2 | 11/2012 | Such et al. |
| 2002/0082489 A1 | 6/2002 | Casciani et al. |
| 2003/0122749 A1 | 7/2003 | Booth, Jr. et al. |
| 2003/0236647 A1 | 12/2003 | Yoon et al. |
| 2005/0049468 A1 | 3/2005 | Carlson et al. |
| 2005/0083272 A1* | 4/2005 | Kimura .................... 345/77 |
| 2005/0267346 A1 | 12/2005 | Faber et al. |
| 2006/0195026 A1 | 8/2006 | Casciani et al. |
| 2006/0195027 A1 | 8/2006 | Casciani et al. |
| 2006/0211929 A1 | 9/2006 | Casciani et al. |
| 2006/0227840 A1* | 10/2006 | Spoonhower et al. .......... 372/64 |
| 2007/0060809 A1 | 3/2007 | Higgins |
| 2007/0129613 A1* | 6/2007 | Rochester et al. ............ 600/310 |
| 2007/0185393 A1 | 8/2007 | Zhou et al. |
| 2007/0282178 A1 | 12/2007 | Scholler et al. |
| 2008/0108887 A1 | 5/2008 | Higgins |
| 2008/0139906 A1 | 6/2008 | Bussek |
| 2008/0234560 A1 | 9/2008 | Nomoto et al. |
| 2008/0242958 A1 | 10/2008 | Al-Ali et al. |
| 2008/0255433 A1 | 10/2008 | Prough et al. |
| 2009/0216096 A1* | 8/2009 | Bloom et al. ................ 600/322 |

FOREIGN PATENT DOCUMENTS

| | | |
|---|---|---|
| CN | 1223843 C | 10/2005 |
| DE | 3516338 | 11/1986 |
| DE | 3703458 | 8/1988 |
| DE | 19640807 | 9/1997 |
| EP | 0127947 | 12/1984 |
| EP | 0204259 | 12/1986 |
| EP | 0531631 | 3/1993 |
| EP | 0724860 | 8/1996 |
| EP | 793942 | 9/1997 |
| JP | H03170866 | 7/1991 |
| JP | 5049625 | 3/1993 |
| JP | 06014906 | 1/1994 |
| JP | 7236625 | 9/1995 |
| JP | 11019074 | 1/1999 |
| JP | 2000237170 | 9/2000 |
| JP | 2004159810 | 6/2004 |
| JP | 2004329406 | 11/2004 |
| JP | 2004337605 | 12/2004 |
| JP | 2004351107 | 12/2004 |
| JP | 2005095581 | 4/2005 |
| JP | 2005125106 | 5/2005 |
| JP | 2005278758 | 10/2005 |
| JP | 2006061566 | 3/2006 |
| JP | 2006075354 | 3/2006 |
| JP | 2006081703 | 3/2006 |
| JP | 2006212161 | 8/2006 |
| JP | 3818211 | 9/2006 |
| JP | 2006239267 | 9/2006 |
| JP | 2006297125 | 11/2006 |
| JP | 2006325766 | 12/2006 |
| JP | 2006326153 | 12/2006 |
| JP | 2007020836 | 2/2007 |
| JP | 2007117641 | 5/2007 |
| JP | 3939782 | 7/2007 |
| JP | 3944448 | 7/2007 |
| JP | 2007167184 | 7/2007 |
| JP | 2007190122 | 8/2007 |
| JP | 2007196001 | 8/2007 |
| JP | 2007259918 | 10/2007 |
| JP | 2007330708 | 12/2007 |
| JP | 4038280 | 1/2008 |
| JP | 2008110108 | 5/2008 |
| WO | 8909566 | 10/1989 |
| WO | 9111137 | 8/1991 |
| WO | WO9316629 | 9/1993 |
| WO | WO9749330 | 12/1997 |
| WO | 9947039 | 9/1999 |
| WO | 0059374 | 10/2000 |
| WO | WO2005007215 | 1/2005 |
| WO | 2005010568 | 2/2005 |
| WO | WO2005099568 | 10/2005 |
| WO | WO2006097910 | 9/2006 |

OTHER PUBLICATIONS

Schulz, Christian Eric; "Design of a Pulse Oximetry Sensor Housing Assembly," California State University Master's Thesis, UMI Dissertation Services, UMI No. 1401306, (May 2000) 63 pages.

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary.

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

* cited by examiner

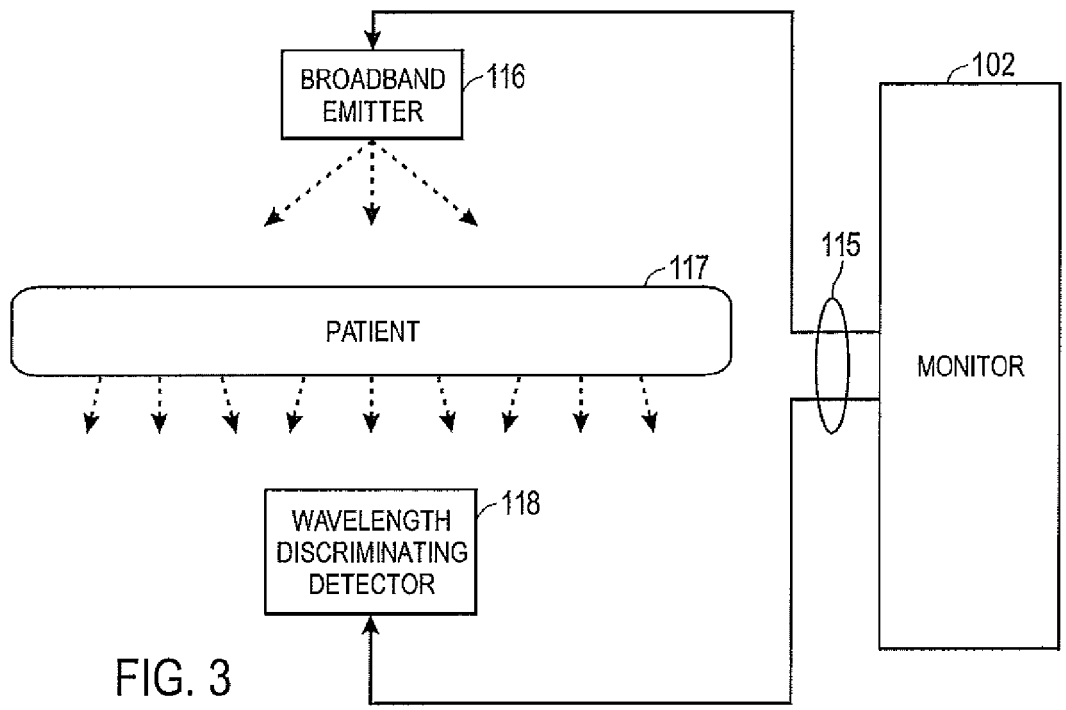
FIG. 3
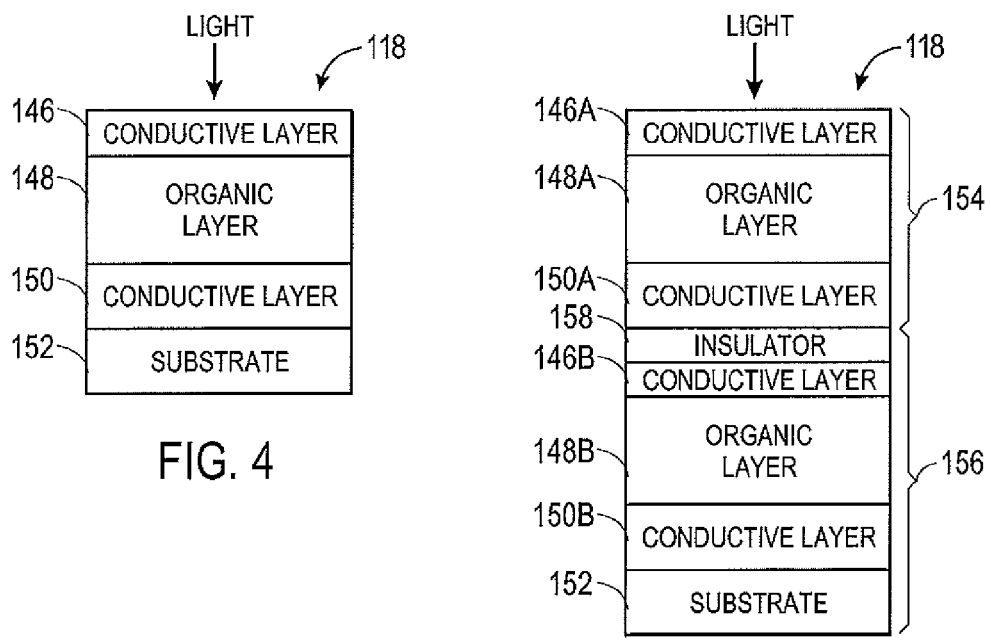
FIG. 4
FIG. 5

ORGANIC LIGHT EMITTING DIODES AND PHOTODETECTORS

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

The light sources utilized in pulse oximeters are typically selected based on their ability to transmit light at specific wavelengths so that the absorption and/or scattering of the transmitted light in a patient's tissue may be properly determined. This may preclude the use of a multitude of readily available, and typically less costly, light sources that transmit light at multiple wavelengths.

BRIEF DESCRIPTION OF THE DRAWINGS

Advantages of the disclosure may become apparent upon reading the following detailed description and upon reference to the drawings in which:

FIG. 3 illustrates a simplified block diagram of a pulse oximeter in FIG. 1, according to a second embodiment;

FIG. 4 illustrates a simplified block diagram of a detector of the pulse oximeter of FIG. 3, according to a first embodiment;

FIG. 5 illustrates a simplified block diagram of a detector of the pulse oximeter of FIG. 3, according to a second embodiment.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Sensors for pulse oximetry or other applications utilizing spectrophotometry are provided therein that include the use of broadband emitters that emit light at in a range of wavelengths. This transmitted light may be received by a detector that selectively detects one or more wavelengths of light based on physical characteristics in the detector. These characteristics may include dopants, such as dyes, that modify the detection abilities of organic material in the detector. In one embodiment, the detector may include one or more organic light emitting diodes (OLEDs), biased to operate as photodetectors and doped to detect specific wavelengths of light. In another embodiment, multiple detectors each with a single OLED may each be able to generate signals based on the light at a specified wavelength received from the broadband emitter, and transmit the generated signals across independent channel lines associated with each of the multiple detectors. A monitor in the pulse oximeter system may receive the signals and calculate physiological parameters of a patent based on the signals without having to demodulate the received signals first.

Figure 1:
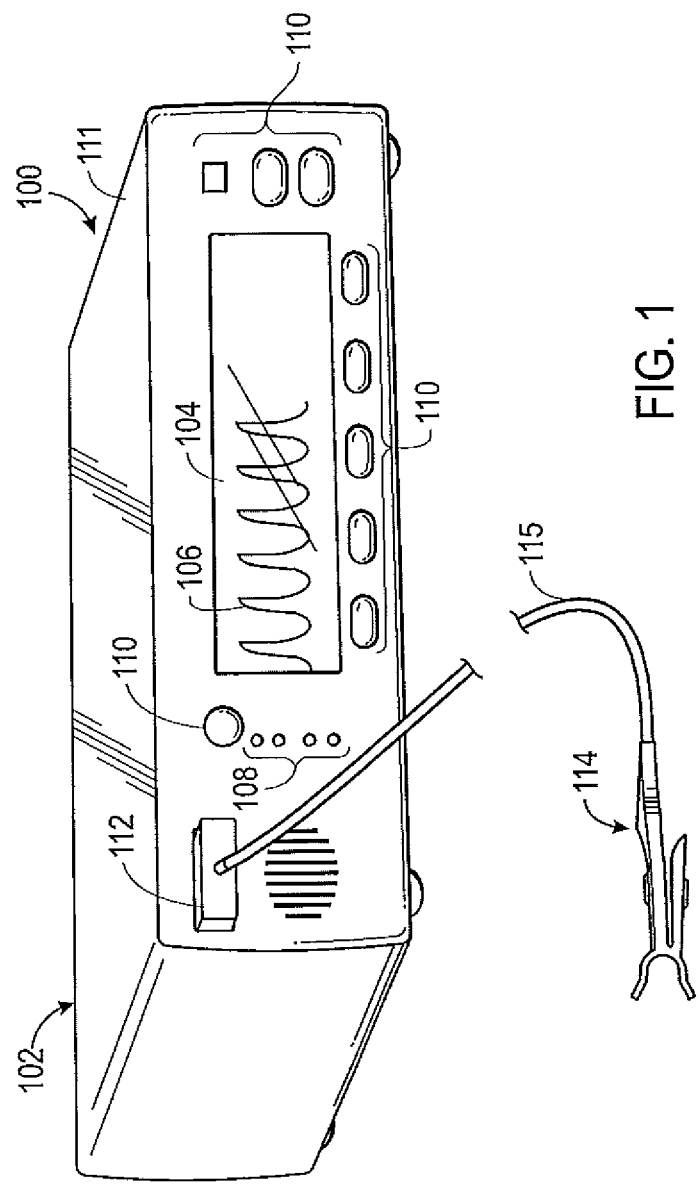
FIG. 1 illustrates a perspective view of a pulse oximeter in accordance with an embodiment.

Turning to FIG. 1, a perspective view of a medical device is illustrated in accordance with an embodiment. The medical device may be a pulse oximeter 100. The pulse oximeter 100 may include a monitor 102, such as those available from Nellcor Puritan Bennett LLC. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a sensor port 112. The sensor port 112 may allow for connection to an external sensor 114, via a cable 115 which connects to the sensor port 112. The sensor 114 may be of a disposable or a non-disposable type. Furthermore, the sensor 114 may obtain readings from a patient, which can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient.

Figure 2:
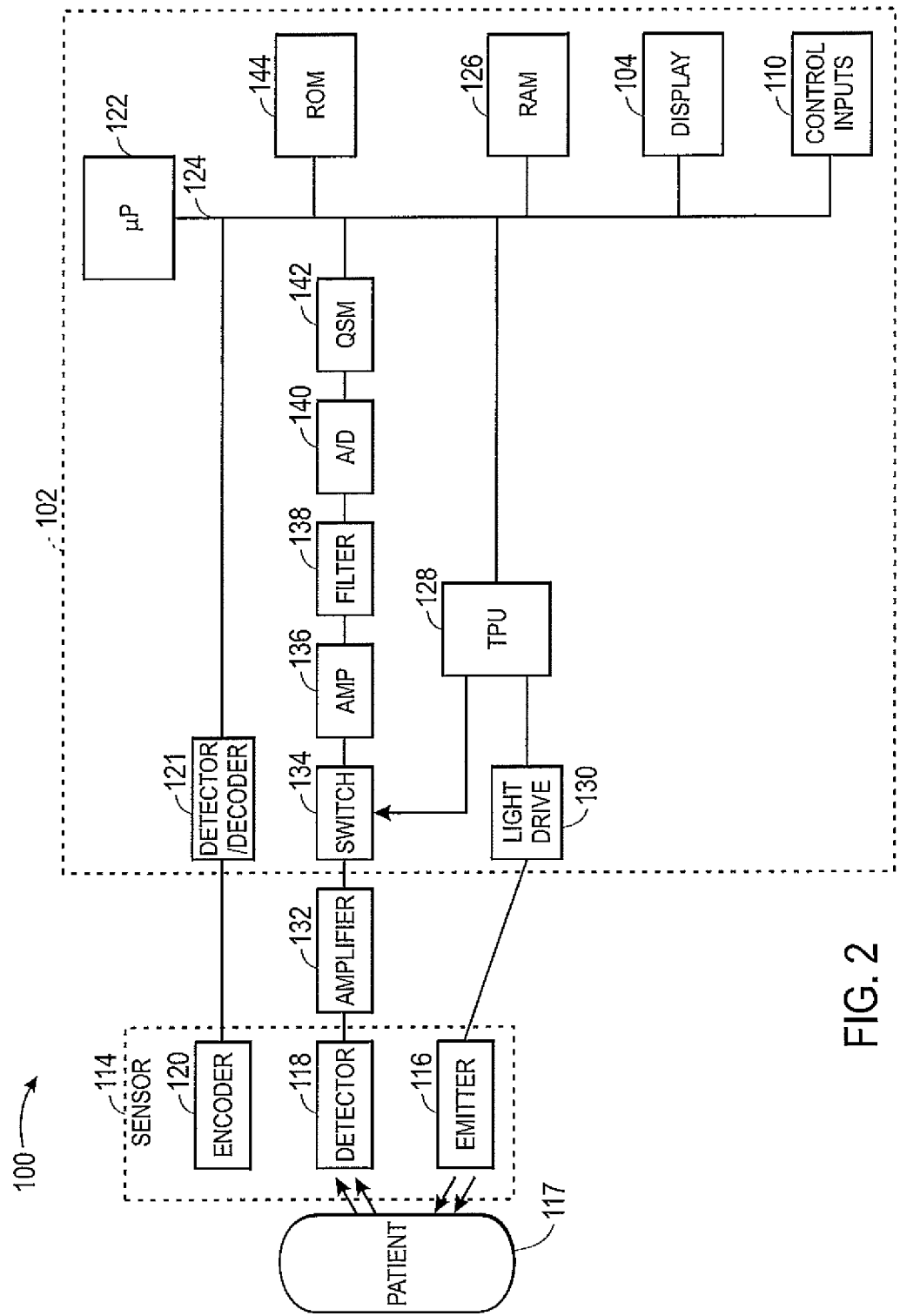
FIG. 2 illustrates a simplified block diagram of a pulse oximeter in FIG. 1, according to an embodiment.

Turning to FIG. 2, a simplified block diagram of a pulse oximeter 100 is illustrated in accordance with an embodiment. Specifically, certain components of the sensor 114 and the monitor 102 are illustrated in FIG. 2. The sensor 114 may include an emitter 116, a detector 118, and an encoder 120. It should be noted that the emitter 116 may be capable of emitting at least two wavelengths of light, e.g., RED and infrared (IR) light, into the tissue of a patient 117 to calculate the patient's 117 physiological characteristics, where the RED wavelength may be between about 600 nanometers (nm) and about 700 nm, and the IR wavelength may be between about 800 nm and about 1000 mm. A single broadband light source may be used as the emitter 116, whereby the broadband light source may transmit light at various wavelengths, including the RED and IR wavelengths, for use in measuring, for example, oxygen saturation, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 118 may be capable of detecting light at various intensities and wavelengths. In operation, light enters the detector 118 after passing through the tissue of the patient 117. The detector 118 may convert the light at a given intensity, which may be directly related to the absorbance and/or reflectance of light in the tissue of the patient 117, into an electrical signal. That is, when more light at a certain wavelength is absorbed or reflected, less light of that wavelength is typically received from the tissue by the detector 118. After converting the received light to an electrical signal, the detector 118 may send the signal to the monitor 102, where physiological characteristics may be calculated based at least in part on the absorption of light in the tissue of the patient 117. As will be described below with respect to FIGS. 3-6, the detector 118 may include one or more doped OLEDs for detecting specific wavelengths of light transmitted from the emitter 116.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's physiological characteristics. The encoder 120 may, for instance, be a memory on which one or more of the following information may be stored for communication to the monitor 102: the type of the sensor 114; the wavelengths of light detected by the detector 118; and the proper calibration coefficients and/or algorithms to be used for calculating the patient's 117 physiological characteristics. The monitor 102 may also include a detector/decoder 121 that may receive signals from the encoder 120. Furthermore, the detector/decoder 121 may, for instance, decode the signals from the encoder 120 and may provide the decoded information to a processor 122. The decoded signals may provide information to the processor such as the type of the sensor 114 and the wavelengths of light detected by the detector 118 so that proper calibration coefficients and/or algorithms to be used for calculating the patient's 117 physiological characteristics may be selected and utilized by the processor 122.

The monitor 102 may include one or more processors 122 coupled to an internal bus 124. Also connected to the bus may be a RAM memory 126 and a display 104. A time processing unit (TPU) 128 may provide timing control signals to light drive circuitry 130, which controls when the emitter 116 is activated, and if multiple light sources are used, the multiplexed timing for the different light sources. TPU 128 may also control the gating-in of signals from detector 118 through an amplifier 132 and a switching circuit 134. These signals are sampled at the proper time, depending at least in part upon which of multiple light sources is activated, if multiple light sources are used. The received signal from the detector 118 may be passed through an amplifier 136, a low pass filter 138, and an analog-to-digital converter 140 for amplifying, filtering, and digitizing the electrical signals the from the sensor 114. The digital data may then be stored in a queued serial module (QSM) 142, for later downloading to RAM 126 as QSM 142 fills up. In an embodiment, there may be multiple parallel paths of separate amplifier, filter, and A/D converters for multiple light wavelengths or spectra received.

In an embodiment, based at least in part upon the received signals corresponding to the light received by detector 118, processor 122 may calculate the oxygen saturation using various algorithms. These algorithms may use coefficients, which may be empirically determined, and may correspond to the wavelengths of light used. The algorithms may be stored in a ROM 144 and accessed and operated according to processor 122 instructions.

FIG. 3 illustrates an embodiment that may include a broadband emitter 116 as well as a wavelength discriminating detector 118. Unlike a typical sensor that may include a first emitter that may transmit light in a visible frequency, such as 660 nm as well as a second emitter that may transmit light in an infrared (IR) range such as approximately 900 nm, the sensor of FIG. 3 may include a single broadband emitter 116 that may transmit light across multiple wavelengths, e.g., along a continuum. For example, the broadband emitter 116 may be a light emitting diode (LED) or an organic light emitting diode (LED), either of which may transmit light across a continuum of wavelengths. Examples of the transmittable wavelengths may include light between, for example, 400 nm and 900 nm. As such, the broadband emitter 116 may transmit light of wavelengths for across both visible and infrared wavelengths. Accordingly, processes such as binning, which may be defined as the process of selecting LEDs that may transmit at specific frequencies, such as 660 nm and 900 nm, may be avoided. Because the LEDs used for the emitter 116 do not have to be binned to perform at a certain wavelength, more LEDs may be available for use in the system illustrated in FIG. 3. That is, broadband emitters, such as LEDs, are no longer excluded from use because of an inability to transmit light at certain peak wavelength ranges used by the monitor 102.

Instead, the wavelength discriminating detector 118 may be utilized to, for example, detect only a single wavelength or a range of red light (between the total range of red light from about 600-700 nm) that passes into the detector 118. Similarly, the wavelength discriminating detector 118 may alternatively and/or additionally be utilized to, for example, detect only a single wavelength or a range of IR light (between a range of IR light from about 700 nm to 1400 nm). Thus, through use of the wavelength discriminating detector 118, the light transmitted from the broadband emitter 116 may be selectively detected so that specified single wavelengths or specified ranges of light, transmitted from the emitter 116, are detected for use in determining physiological parameters of the patient 117.

In operation, the broadband emitter 116 may receive input signals from monitor 102. These input signals may be used to activate the broadband emitter 116 so that light may be generated via the emitter 116. As light is generated from the emitter 116, it may pass through the patient 117 for detection by the wavelength discriminating detector 118. The transmitted light may be scattered and/or absorbed by the patient 117, and may subsequently exit the patient 117. Upon exiting the patient 117, the light may be received by the wavelength discriminating detector 118. At least one wavelength of light from the received light, which may include both visible and IR wavelength light, may be detected. Additionally, the wavelength discriminating detector 118 may generate electrical signals corresponding to the detected light, based upon the configuration of the wavelength discriminating detector 118 (i.e., based on the wavelengths of light the wavelength discriminating detector 118 is capable of detecting). For example, the wavelength discriminating detector 118 may detect visible light in the optical range of about 660 nm passing through the patient 117. Alternatively, and/or additionally, the wavelength discriminating detector 118 may detect, for example, light at about 900 nm passing through the patient 117. Regardless of which light is detected, the wavelength discriminating detector 118 may generate electrical signals corresponding to the received light.

To aid in the interpretation of these signals, a demodulator may be utilized. The demodulator may interpret the various received signals as, for example, corresponding to light in either the red or infrared spectrum. This demodulation may, for example, take place in the monitor 102 in, for example, the detector/decoder 121 and/or in the processor 122. That is, the received signals at detector 118 may be transmitted via cable 115 to the monitor 102 for processing, which may include demodulation of the signals transmitted from the wavelength discriminating detector 118. Based on these demodulated signals, for example, the oxygenation of the blood of the patient 117 may be determined in accordance with known techniques.

FIG. 4 illustrates an embodiment of the wavelength discriminating detector 118 discussed above. The wavelength discriminating detector 118 may be, for example, a reverse biased organic light emitting diode (OLED). Accordingly, the wavelength discriminating detector 118 may include a first conductive layer (cathode) 146, an organic layer 148, a second conductive layer (anode) 150, and a substrate 152. The cathode 146, the organic layer 148, and the anode 150 may be deposited onto the substrate 152 by any suitable technique, including sputtering, thermal vapor phase deposition, or electron beam deposition.

The cathode 146 may be an electrode that allows current to flow through the organic layer 148. The cathode 146 may approximately 50 nm to 100 nm thick. Furthermore, the cathode 146 may be transparent and may be formed from metal oxides such as indium tin oxide (ITO), and indium zinc oxide (IZO). The cathode 146 may also be coupled to the organic layer 148.

The organic layer 148 may include organic molecules, such as poly[2-methoxy-5-(2'-ethylhexyloxy)-p-phenylene vinylene (MEH-PPV) or polymers and may be approximately 150 nm to 300 nm thick. The organic layer 148 may include organic material that may emit and/or detect light at a certain wavelength and/or at a certain range. In one embodiment, the organic layer 148 may include polyfluorene and/or polyaniline. The organic layer 148 may include an electron transport (n-type) layer adjacent to the cathode 146, an emissive layer coupled to the electron transport layer, and a hole injection (p-type) layer such as, Poly(3,4-ethylenedioxythiophene) poly(styrenesulfonate) (PEDOT:PSS) adjacent both the emissive layer and the anode 150. Each of these layers may be approximately 50 nm to 100 nm and, in conjunction, may form the organic layer 148.

As described above, the anode 150 may be coupled to the organic layer 148, specifically to the hole injection layer of the organic layer 148. The anode 150, similar to the cathode 146, may be an electrode that allows current to flow through the organic layer 148. The anode 150 may approximately 100 nm to 150 nm thick. Furthermore, the anode 150 may be transparent and may be formed from metal oxides such as indium tin oxide (ITO). Additionally, the anode 150 may be coupled to the substrate 152.

The substrate 152 may be a material on which the layers 146-150 may be deposited (i.e., the substrate 152 may support the layers 146-150). The substrate 152 may be approximately 100 nm to 300 nm thick and may be made of glass or plastic. Additionally, the substrate 152 may be flexible and, as such, may include acrylic. The use of acrylic may allow for the wavelength discriminating detector 118 to be malleable and formable as desired by a user.

The wavelength discriminating detector 118 described above may include an OLED. As known in the art, when a forward bias is applied to an OLED (i.e., negative voltage at the cathode 146 and positive voltage at the anode 150), electrons move onto the organic layer 148 from the cathode 146 while positive charges (i.e., holes) move into the organic layer 148 from the anode 150. The electrons and holed may combine in the organic layer 148, for example, in the emissive layer, to produce photons (i.e., light). The wavelength of the light produced may be affected by the electronic properties of the organic material in which the photons are generated and/or by dopants that may be introduced into the organic layer 148. For example, infrared light may be emitted from an OLED by introducing ions such as neodymium or erbium to the organic layer 148. Accordingly, by doping the organic layer 148, light of a particular wavelength may be generated when the OLED is forward biased. However, light emitting properties of the OLED are not necessarily desirable in the wavelength discriminating detector 118. Instead, it may be advantageous to utilize the OLED as a photodiode or photodetector, which may be accomplished by applying a reverse bias to the OLED, as described below.

As mentioned above, photons in the photoluminescence band are generated from the organic layer 148 under forward bias, (i.e., a positive voltage is applied between the anode 150 and the cathode 146). However, for the OLED to operate as a photodetector in detector 118, the OLED may be reverse biased (i.e., positive voltage at the cathode 146 and negative voltage at the anode 150). For example, when the OLED is reverse biased at approximately 5 v, (i.e., a negative voltage is applied between the anode 150 and the cathode 146), the OLED may operate as a photodiode, or photodetector, for detecting light at wavelengths in the absorption band of the detector. That is, the organic layer 148 may contain chromophores, detecting light at wavelengths in the absorption band when the OLED in 118 is reverse biased.

Based on the electronic and optical properties of the organic layer 148, and based on dopants or dyes introduced into the organic layer 148, the organic layer 148 will operate to detect light at a wavelengths in the absorption band of the organic layer to what would be emitted in the photoluminescence band if the OLED was in a forward biased mode. For example, when an OLED doped with ions such as neodymium or erbium is operated in a reverse bias mode, infrared light may be detected by the OLED. This effect may be produced as a result of the reverse bias of the OLED. For example, a negative charge at the anode 150 generates an electron region in the organic layer 148 while a positive charge at the cathode 146 generates a hole region in the organic layer 148. Between the electron and hole regions may be a charge depletion region, (typically located in the region previously termed the "emissive layer"). When a photon of light in the absorption band of the organic emission layer strikes the charge depletion region, energy is imparted to the charge depletion region, resulting in an electron/hole pair being generated. This electron/hole pair may be swept from the charge depletion region, with the electron flowing towards the anode 150 and the hole flowing towards the cathode 146. This, in effect, generates a current, which, in turn, may indicate the wavelength and strength of light that was received by the wavelength discriminating detector 118. In this manner, only light of a particular wavelength (or range of wavelengths) is detected by the OLED, causing the wavelength discriminating detector 118 to operate as both a photodetector and an optical filter without additional hardware. Thus, the photoluminescence spectrum or band may determine the emission color, while the absorption may determine the detection wavelength selection.

The wavelength discriminating detector 118 described above may operate to isolate and detect light at a particular wavelength or particular range of wavelengths. However, it may be advantageous to isolate and detect light at two or more wavelengths or two or more ranges of wavelengths. Accordingly, FIG. 5 illustrates an embodiment of the wavelength discriminating detector 118 whereby light at two distinct wavelengths may be detected.

The wavelength discriminating detector 118 of FIG. 5 may include a first OLED 154 and a second OLED 156 in a stacked configuration with an insulator 158 therebetween. The insulator 158 may provide an insulative barrier between the first OLED 154 and the second OLED 156. The insulator 158 may have a thickness of approximately 25 nm and may include a dielectric material such as aluminum oxide or silicon nitride. It should be noted that the use of the insulator 158 may be optional in the wavelength discriminating detector 118.

Both the first OLED 154 and the second OLED 156 may operate under a reverse bias of approximately 5 v. This reverse bias may cause the OLEDs 154 and 156 to operate as photodetectors. However, OLED 154 may be doped with a different dye than OLED 156. This may allow OLED 154 to detect light at a different frequency than OLED 156. For example, OLED 154 may be doped with ions such as neodymium or erbium such that infrared light may be detected by the reverse biased OLED 154. Additionally, OLED 156 may be doped with dyes that emit that have a absorption peak at 660 nm (red) may be detected by the OLED 156. Thus, currents (detection signals) generated by the OLEDs 154 and 156 may be transmitted to, for example, a demodulator for aid in the interpretation of these signals. The demodulator may interpret the various received signals as, for example, corresponding to light in either the red or infrared spectrum. This demodulation may, for example, take place in the monitor 102. In this manner, a single wavelength discriminating detector 118 may detect multiple discrete (specific) wavelengths for determination of multiple physiological parameters of a patient 117.

Figure 6:
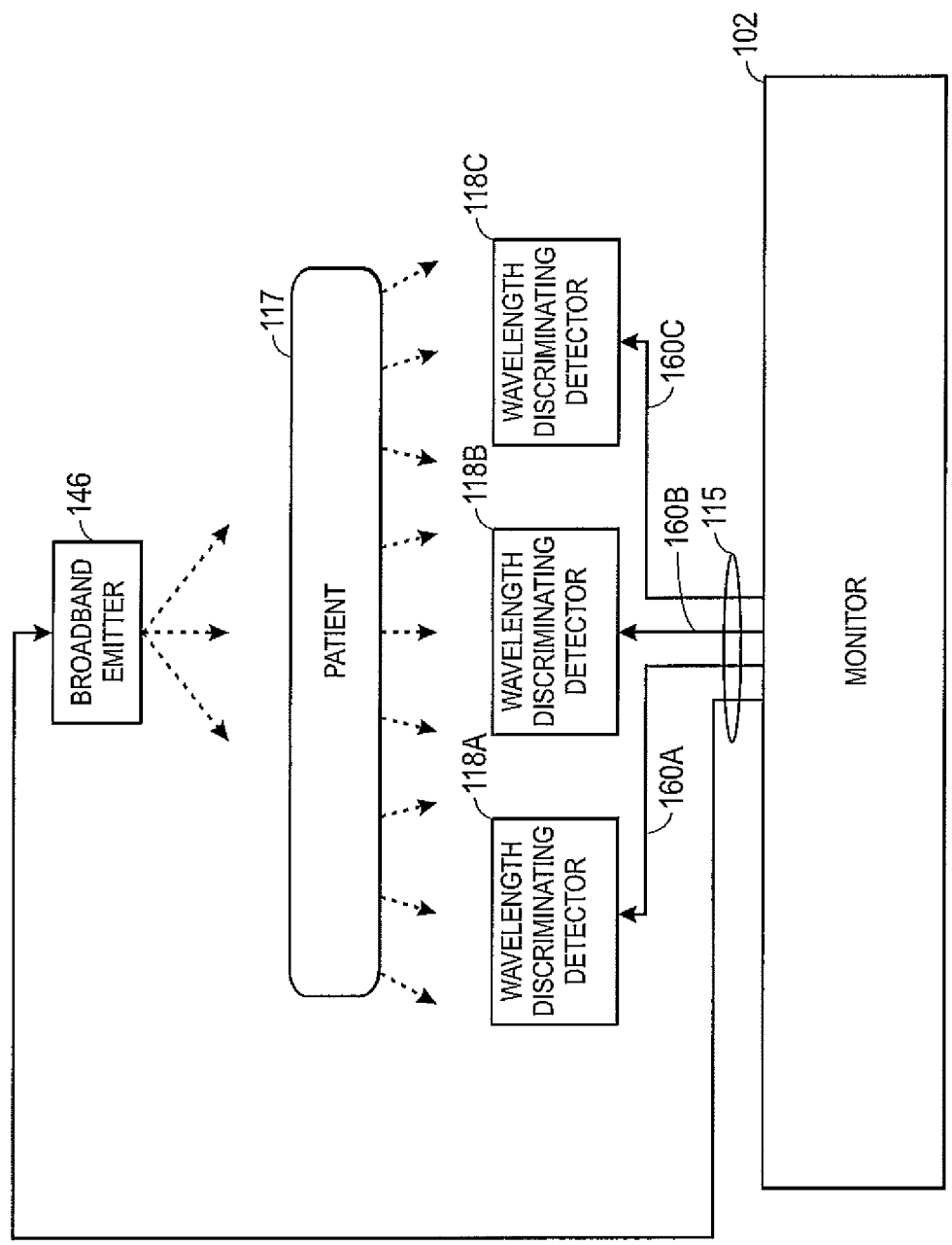
FIG. 6 illustrates a simplified block diagram of a pulse oximeter in FIG. 1, according to a third embodiment.

While the wavelength discriminating detector 118 of FIGS. 3 and 5 were described as being utilized in conjunction with a demodulator, at least one alternate embodiment of a pulse oximeter 100 may be implemented without the use of a demodulator. FIG. 6 illustrates one such configuration of a pulse oximeter 100 that may operate without a demodulator even as multiple wavelengths may be simultaneously monitored via a detector array.

The pulse oximeter 100 of FIG. 6 may include a sensor 114 with a single broadband emitter 116 as well as three wavelength discriminating detectors 118A, 118B, and 118C connected to the monitor 102 via a cable 115. Utilizing multiple detectors, such as wavelength discriminating detectors 118A, 118B, and 118C, may be beneficial in that the multiple wavelength discriminating detectors 118A, 118B, and 118C may each utilize an independent signal path to transmit signals corresponding to received light, eliminating demodulation of the signals. Use of multiple detectors may also be beneficial when multiple physiological parameters of the patient 117 are to be monitored simultaneously without the use of a demodulator. Furthermore, it should be noted that while three wavelength discriminating detectors 118A, 118B, and 118C are illustrated in FIG. 6, greater than three or less than three wavelength discriminating detectors may be utilized in conjunction with a sensor 114 as described below.

The broadband emitter 116 may transmit light across a given range of wavelengths that may include, for example, both visible and IR light. This light may pass into patient 117, and may pass from patient 117 to each of the wavelength discriminating detectors 118A, 118B, and 118C. As discussed below, the wavelength discriminating detectors 118A, 118B, and 118C may each detect separate wavelengths of light, and thus, may generate separate signals corresponding to the received light. Accordingly, a demodulator is not required for use in conjunction with the system of FIG. 6 because the signals corresponding to, for example, visible and IR light, are already separated from each other via the independent wavelength discriminating detectors 118A, 118B, and 118C.

The first wavelength discriminating detector 118A may detect light of a given wavelength, such as light in the red spectrum around 660 nm, or a given range of wavelengths from, for example, 630 nm to 690 nm. Similarly, the second detector 118B may detect light of a given wavelength, such as light in the infrared spectrum around 900 nm, or a given range of wavelengths from, for example, 870 nm to 930 nm. Finally, the third detector 118C may detect light of a given wavelength, such as light at a wavelength of approximately 550, or a given range of wavelengths from, for example, 520 nm to 580 for use in determining, for example, hematocrit levels in the blood of a patient 117.

In this manner, a single broadband emitter 116 may be utilized to transmit light to a plurality of wavelength discriminating detectors 118A, 118B, and 118C, wavelength discriminating detectors 118A, 118B, and 118C, each dedicated to allow certain wavelengths of light to be detected. Thus, each of the wavelength discriminating detectors 118A, 118B, and 118C may each be able to receive light that may be utilized in detecting specific physiological parameters according to the light received.

Moreover, by utilizing multiple wavelength discriminating detectors 118A, 118B, and 118C, each with its own respective channel line 160A, 160B, and 160C to the monitor 102, the monitor 102 may receive electrical signals corresponding to specific values of the patient 117 that may be utilized in calculation of specific physiological parameters of the patient 117 simultaneously. That is, the detectors 118A may comprise a three-channel detector array that allows for determination of the oxygen saturation of the patient 117, the hematocrit levels of the patient 117, and/or other physiological readings of the patient 117, simultaneously and without the need for a demodulator. That is, each channel line 160A, 160B, and 160C may transmit electrical signals corresponding to each of the above-referenced values for calculation by the monitor 102. As such, because the received signals may be on different channel lines 160A, 160B, and 160C, the signal transmitted from the wavelength discriminating detectors 118A, 118B, and 118C to the monitor 102 may not need to be demodulated. Accordingly, this may reduce the cost and complexity of the monitor 102.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A spectrophotometric sensor, comprising:
    a sensor body;
    a light emitting component disposed on the sensor body; and
    a wavelength discriminating detector disposed on the sensor body, wherein the wavelength discriminating detector comprises a first organic light emitting diode and a second organic light emitting diode in a stacked configuration with respect to the first organic light emitting diode, wherein each of the first organic light emitting diode and the second organic light emitting diode is configured to detect light at a distinct wavelength.

2. The spectrophotometric sensor of claim 1, wherein the light emitting component emits light along a continuum.

3. The spectrophotometric sensor of claim 1, wherein each of the first organic light emitting diode and the second organic light emitting diode comprise:
    an organic layer;
    a substrate layer; and
    one or more transparent electrode layers.

4. The spectrophotometric sensor of claim 3, wherein the organic layer comprises a doped organic layer.

5. The spectrophotometric sensor of claim 4, wherein the doped organic layer comprises a chromophore.

6. The spectrophotometric sensor of claim 4, wherein the doped organic layer of the organic light emitting diode is doped with a different dye than the doped organic layer of the second organic light emitting diode.

7. The spectrophotometric sensor of claim 3, wherein the substrate layer comprises an acrylic.

8. The spectrophotometric sensor of claim 3, wherein the one or more transparent electrode layers comprises indium tin oxide.

9. The spectrophotometric sensor of claim 1, comprising an insulator positioned between the organic light emitting diode and the second organic light emitting diode.

10. A pulse oximetry system comprising:
    a pulse oximetry monitor; and
    a sensor assembly configured to be coupled to the monitor, the sensor assembly comprising:
        a broadband light emitter adapted to transmit light across a range of wavelengths;
        a plurality of wavelength discriminating detectors adapted to receive the light from the broadband emitter, wherein each of the plurality of wavelength discriminating detectors is adapted to receive transmitted light across the range of wavelengths and to detect light transmitted from the broadband light emitter at a specific wavelength or at a subset of the range of wavelengths, and wherein each of the plurality of wavelength discriminating detectors comprises an organic light emitting diode;
    a first channel line configured to couple a first wavelength discriminating detector of the plurality of wavelength discriminating detectors to the monitor; and
    a second channel line configured to couple a second wavelength discriminating detector of the plurality of wavelength discriminating detectors to the monitor, wherein the second channel line is independent from the first channel line.

11. The pulse oximetry system, as set forth in claim 10, wherein the specific wavelength or subset of the range of wavelengths differs for each of the plurality wavelength discriminating detectors.

12. The pulse oximetry system, as set forth in claim 10, wherein the first wavelength discriminating detector of the plurality of wavelength discriminating detectors is configured to detect a specific wavelength or subset of wavelengths in a red range suitable for pulse oximetry measurements.

13. The pulse oximetry system, as set forth in claim 12, wherein the second wavelength discriminating detector of the plurality of wavelength discriminating detectors is configured to detect a specific wavelength or subset of wavelengths in an infrared range suitable for pulse oximetry measurements.

14. The pulse oximetry system, as set forth in claim 13, wherein a third wavelength discriminating detector of the plurality of wavelength discriminating detectors is configured to detect a specific wavelength or subset of wavelengths in a range suitable for determining hematocrit levels.

15. A physiological sensor comprising:
    a broadband light emitter adapted to transmit light across a range of wavelengths;
    a plurality of wavelength discriminating detectors, wherein each of the plurality of wavelength discriminating detectors comprises an organic light emitting diode configured to receive the light from the broadband emitter and to detect light transmitted from the broadband light emitter at a specific wavelength or at a subset of the range of wavelengths, wherein each of the plurality of wavelength discriminating detectors is coupled to an independent signal path to transmit signals corresponding to the received light to a monitor.

16. The physiological sensor of claim 15, wherein the organic light emitting diode comprises a dopant of neodymium or erbium.

17. The physiological sensor of claim 15, wherein the specific wavelength is approximately 660 nm.

18. The physiological sensor of claim 15, wherein the subset of the range of wavelengths is approximately 630 nm to 690 nm.

19. The physiological sensor of claim 15, comprising a second organic light emitting diode comprising a dopant of red fluorescent dye.

20. The physiological sensor of claim 19, wherein the second organic light emitting diode is adapted to detect light transmitted from the broadband light emitter at a specific wavelength of approximately 900 nm or at a subset of the range of wavelengths of approximately 870 nm to 930 nm.

* * * * *